United States Patent [19]

Herman

[11] Patent Number: 4,738,680
[45] Date of Patent: Apr. 19, 1988

[54] LASER EDGE LENS

[76] Inventor: Wesley K. Herman, 5461 La Sierra, Dallas, Tex. 75231

[21] Appl. No.: 881,856

[22] Filed: Jul. 3, 1986

[51] Int. Cl.⁴ .................................................. A61F 2/16
[52] U.S. Cl. ................................................................ 623/6
[58] Field of Search .................................................. 623/6

[56] References Cited

U.S. PATENT DOCUMENTS

| 4,494,254 | 1/1985 | Lopez | 623/6 |
| 4,562,600 | 1/1986 | Ginsberg et al. | 623/6 |
| 4,573,998 | 3/1986 | Mazzocco | 623/6 |

FOREIGN PATENT DOCUMENTS 1103399 5/1955 France .................................. 623/6

Primary Examiner—Ronald L. Frinks

[57] ABSTRACT

An intraocular lens is provided for implantation into the posterior chamber of the eye following extracapsular cataract surgery. The lens body includes a convex posterior surface having an optic area positioned in direct apposition to the posterior capsular membrane. The curvature of the posterior surface of the lens is fixed and power modifications are made by changing the curvature anterior optical surface of the lens body. The circumferential edge of the lens body is angled posteriorly to provide an annular space outside the optic area of the lens for laser or knife surgery frequently necessary after the lens implantation by extra capsular technique.

18 Claims, 1 Drawing Sheet

U.S. Patent  Apr. 19, 1988  4,738,680
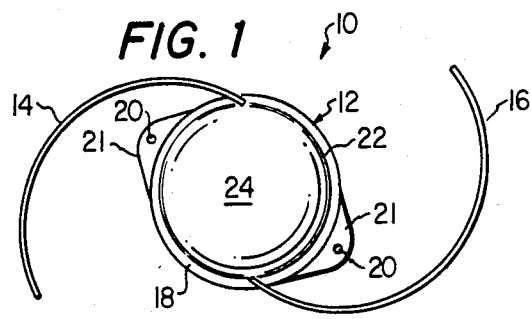
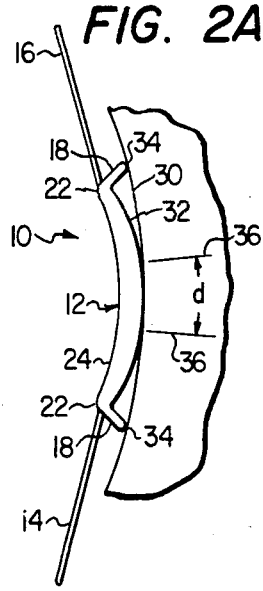 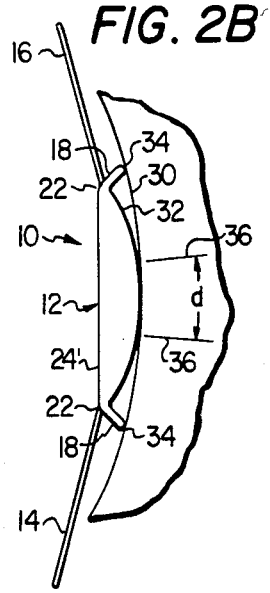 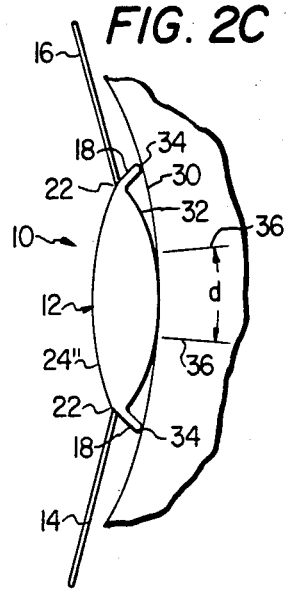
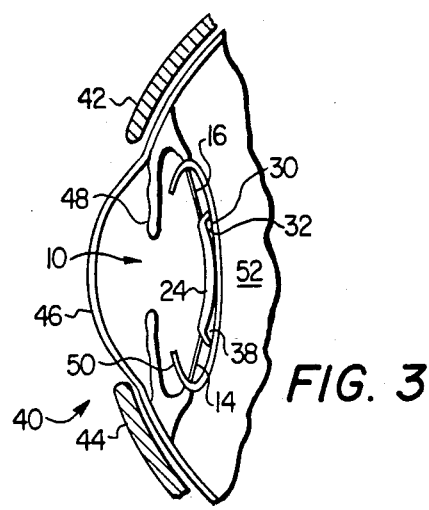

LASER EDGE LENS

TECHNICAL FIELD

This invention relates to an intraocular lens intended for implant in the posterior chamber of the eye following extracapsular cataract extraction.

BACKGROUND ART

A cataract is a cloudiness or opacity which develops in the lens of the eye which is normally clear and transparent. A person with impaired vision due to a cataract may have his vision improved through a combination of cataract surgery and proper corrective lenses.

An ophthalmologic surgeon may elect one of several different surgical procedures for removing a lens that has a cataract. Intracapsular cataract extraction is a technique for the removal of the entire cataract, including its capsule, in one piece. Extracapsular cataract extraction and phacoemulsification and aspiration are two surgical technique that involve the removal of the opacified portions of the lens, while the clear posterior capsule which was the original support for the lens is left in place.

Intracapsular or extracapsular extraction eliminates the cloudiness or opacity caused by the cataract, but light entering the eye is now unfocused since the lens has been removed. Light entering the eye may be focused by an intraocular lens.

Ophthalmologic surgeons now generally recognize that it is better optically an physiologically to implant the intraocular lens into the posterior chamber of the eye. Intraocular lens implants have also been done in the anterior chamber in which the lens is implanted forward of or mounted to the iris. Implantation of the intraocular lens behind the pupil has been found to cause fewer secondary problems following extracapsular surgery, particularly glaucoma and swelling of the eye called cystoid macular edema.

Intraocular lens implants into the posterior chamber also have been found to have some secondary complications. Nearly half of the patients who have had extracapsular cataract extraction experience some loss of visual function from clouding of the posterior capsule within several months to several years after the initial surgery. In order to restore a patient's visual function, further surgery becomes necessary to make an opening in the posterior capsule with a knife or a laser.

Ophthalmologic surgeons in the past have tried to design intraocular lenses for implant into the posterior chamber that retard the opacification or clouding of the posterior capsule membrane left following the extracapsular cataract extraction. One of the first intraocular posterior chamber lenses designed to retard opacification and to facilitate discission of the membrane is diclosed in U.S. Pat. No. Re. 31,626, issued on July 10, 1984 to Kenneth J. Hoffer. Hoffer designed a lens having a convex-plano relationship where the power is put in the front or anterior surface of the lens. The rear or posterior surface has a ridge intended to prevent the lens cells from sliding in beneath the ridge, thus retarding opacification. The Hoffer lens had an opening along the circumferencial ridge for insertion of a surgical knife or needle through the opening in the posterior chamber in the space behind the lens, but there is no contact of the lens optic with the posterior capsular membrane.

Another design for an intraocular posterior chamber lens is disclosed in U.S. Pat. No. 4,485,499, issuing to Lawrence D. Castleman. The lens has a convex front face and a generally planar rear face with two parallel projecting members. The projecting members were said to provide a separation or open zone at the visual axis between the lens body and posterior capsule to facilitate corrective discission surgery. Again, this lens does not provide contact of the lens optic with the posterior capsular membrane (PCM).

Yet another design of a posterior intraocular lens is disclosed in U.S. Pat. No. Re. 31,998, reissued on Oct. 8, 1975 to William D. Myers. The Myers lens implant was intended to facilitate laser posterior capsulotomy following extracapsular surgery. In one form, the lens has a front convex surface, and a bridge spaces the generally planar rear surface of the optic forward of the posterior capsule. In a second form, the lens has a convex front surface, but the rear surface optic is concave to provide a space forward of the posterior capsule. This lens also does not provide lens optic contact with the PCM.

It is therefore an object of the present invention to provide an improved intraocular posterior chamber lens that overcomes disadvantages of prior art lenses in retarding opacification following extracapsular cataract extraction and reducing the likelihood of secondary surgical procedures.

It is another object of the invention to provide an improved intraocular posterior chamber lens having a convex rear surface with a constant radius of curvature in direct apposition with the posterior capsule of the eye to improve early visual acuity following cataract extraction and to retard opacification in an area of direct contact of the optic with the PCM.

It is another object of the invention to provide an intraocular posterior chamber lens in which the optic power modification for the lens is achieved by the modification of the anterior or front side of the lens. This will effect less contact of the anterior surface of the intraocular lens implant with the iris, which is a frequent clinical occurence with the above referenced designs.

It is still another object of the invention to provide an improved intraocular posterior chamber lens in which an annular space is provided beneath the lens body and outside the optic zone of the lens implant to facilitate YAG laser surgery or knife discission, which may be required as a secondary surgical procedure sometime after implantation of the intraocular lens.

It is still another object of the invention to provide an improved intraocular posterior chamber lens having an optic and haptic design enabling manufacture of a foldable soft intraocular lens suitable for surgical injection through a small incision into the eye.

DISCLOSURE OF THE INVENTION

According to the present invention, an intraocular lens is provided for implant into the posterior chamber of the eye following extracapsular cataract extraction. The lens has a convex posterior surface for direct apposition with the posterior capsule. The lens is designed to maintain a constant relationship with the posterior capsule and the dioptric power of the lens is fixed for all dioptric ranges posteriorly. Power modification to the lens is achieved by modifications of the front or anterior surface of the lens. The posterior surface of the lens contacts the posterior capsule over a constant area of the posterior capsule to provide improved early visual acuity and to retard opacification by blocking migration of epithelial cells between the posterior capsule and the lens. A circumferential edge portion of the lens is angled posteriorly and terminates in a plane to contact and support the edge of the lens on the surface of the posterior capsule. The circumferential edge region is outside the optic region and the convex posterior surface projects posteriorly beyond the plane of the circumferential edge region, thereby stretching and deforming the posterior capsular membrane into conformity with the convex posterior surface to improve visual acuity. The angled circumferential edge of the lens in combination with the design of the convex rear surface creates an annular space between the lens and the posterior capsule to facilitate any discission of the membrane with a laser or knife. The circumferential edge also serves to block migration of cells beneath the lens. Angled haptics are attached to the edge of the lens for securing it within the posterior capsular membrane.

BRIEF DESCRIPTION OF THE DRAWINGS

A more complete understanding of the present invention and its advantages will be apparent from the following Detailed Description taken in conjunction with the accompanying Drawings in which:

FIG. 1 is a top plan view of one embodiment of the posterior intraocular lens of the present invention;

FIG. 2A is a side elevation view of the lens shown in FIG. 1 with a partially cut away side view of the posterior chamber of the eye;

FIG. 2B is an alternate embodiment of the lens of FIG. 2A in which the lens has a different power modification;

FIG. 2C is an alternate embodiment of the lens of FIG. 2A in which the lens has a different power modification; and FIG. 3 is a cross sectional schematic view of a portion of the human eye showing a lens of the present invention implanted following extracapsular cataract extraction.

DETAILED DESCRIPTION

FIG. 1 illustrates a top plan view of the posterior chamber intraocular lens of the present invention, generally identified by the reference numeral 10. The intraocular lens 10 has a lens body 12 with associated haptic members 14 and 16 attached to the periphery of the lens body 12. Manipulation holes 2 and tabs 21 are not essential to the present invention but may be included to provide the ophthalmologic surgeon with a means to facilitate placement of the lens 12 in the human eye. An edge region 18 is angled posteriorly for lifting the lens body 12 off the posterior capsule in the region outside of the optical zone of the eye. The edge region 18 begins along the circumlinear line 22 where the anterior surface 24 begins to angle posteriorly.

The lens body 12 of the lens 10 would typically be 6 millimeters in diameter. The manipulation holes 20 may be on the order of 0.4 millimeter in diameter.

The lens body 12 of the posterior chamber intraocular lens 10 may be made from polymethylmethacrylate (PMMA). The optic material for the lens body 12 may be made with any other suitable material to create the necessary optics for the patient, but the material selected should be one that is acceptable for use with laser surgery, such as a yttrium aluminum garnet (YAG) laser, for secondary cataract procedures. In addition, the lens body 12 may be made from silicone for use as a soft injectable intraocular lens. The optic design of the intraocular lens 10 and associated haptic design may be particularly suitable for use in a soft injectable lens design.

The lens body 12 of intraocular lens 10 may be manufactured from any of the four principal technologies used for manufacturing intraocular lenses. First, in injection molding, plastic is injected into a mold design for the lens in a liquid state at very high pressure, permitting removal of the lens when it is the solid state. The injection molding technique is one of the oldest and could be used in manufacturing the lens 10 of the present invention. However, a lens made with this technique may be more susceptible to damage from a YAG laser than lenses made from other technologies. In cast molding technology, a lens is made from two halves that are assembled together to form the optic. The lens 10 of the present invention would be particularly suitable for this technique since one half of the cast would have a fixed design, the posterior surface of the lens body 12. The anterior or front half of the lens body 12 has a predetermined shape that determines the optical power of the lens body and could be made to provide any of the various power modifications required for the lens 10. The anterior surface or front half of the lens body could be either concave, plano or convex, as illustrated and further described in FIGS. 2A–C below. In cast molding or injection molding, approximately 20 or 30 front halves could be utilized to cover the desired optic powers for the lens. In lathe technology, the optic or lens body 12 could be cut from a single piece of plastic, and haptics could be inserted into the optic. Individual optic designs could be accomplished by inputting the power requirements on the anterior surface into a computer controlling the lathe operation. The specification of the posterior surface would be constant for all lens powers. Finally, the lens 10 could be made from silicone, or other suitable pliable material. A suitable lens 10 made from silicone would be particularly suitable for use as a lens injected into the eye through a small incision.

The haptics 14, 16 may be made out of polypropylene or Prolene (a trademark of Ethicon, Inc.), extruded PMMA or polyamide. The polyamide material would be suitable for use together with the silicone lens to make an injectable lens 10.

FIG. 2A is a side elevational view of the intraocular lens 10 of the present invention seated on the posterior capsular membrane 30, illustrated in partial cut away, following extracapsular cataract extraction. The optic or lens body 12 has a posterior or rear surface 32 in direct apposition with the posterior capsular membrane 30. The posterior surface 32 has a constant radius of curvature to provide reproducible contact with the posterior capsular membrane 30 of a distance "d" equal to approximately 3.5 millimeters. The distance "d" is within a range of 2.5 to 4.5 millimeters. Thus, the posterior surface 32 of lens body 12 may have a radius of curvature to provide more or less than 3.5 millimeters of contact. Lens body 12 has a front or anterior surface 24 that is concave, which would be the case for commonly used lenses having less than +25 diopter. The circumlinear line 22 defines where the anterior surface 24 begins to extend posteriorly to define the peripheral edge region 18. The edge region 18 extends a predetermined distance at a predetermined angle and lifts the posterior surface 32 of the posterior capsular membrane 30 at a point 34. The haptics 14, 16 postion the lens 10 within the capsule bag and against the posterior capsular membrane 30.

The posteriorly projecting edge region 18 and the design of the convex posterior surface 32 provide an annular space outside the optic region "d" of the lens 10. The annular space is provided between point 34 and point 36 where the posterior surface 32 of the lens is lifted from the concave surface of the posterior capsular membrane 30. The annular space 38 between points 34 and 36 creates a region in which a laser may be used in discission of the posterior capsular membrane 30 in secondary cataract operations. However, the direct apposition of the optic or lens body 12 within the central optical region of the posterior capsular membrane 30 provides improved vision for the patient earlier and retards the opacification which may eventually require secondary cataract surgery following extracapsular cataract extraction. The direct apposition of the convex surface 32 with the posterior capsular membrane 30 capsule stretches the bag and posterior capsule 30 and reduces any wrinkling of the posterior capsular membrane 30. The support of lens 10 between points 34 and at 36 also facilitates opening of the capsule with a laser by the slight tension that is created between these points.

In FIGS. 2B and 2C, the optical power of the intraocular lens of FIG. 2A has been modified by altering the anterior or front surface 24. In FIG. 2B, the lens body 12 has a planar anterior surface 24'. In FIG. 2C, the anterior or front surface 24" has a convex design to further modify the power of the lens body 12. By way of example, the planar anterior surface 24' version with lens body 12 in FIG. 2B may have a total power of +25 diopters and the convex anterior surface 24" version may be for a lens 10 with a total power of +35 diopters. In the lens bodies 12 illustrated in FIGS. 2B and 2C, the convex posterior surface 32 remains unchanged with respect to the posterior capsule 30 of the eye. Power modifications of the lens body 12 may be achieved solely by changing the front or anterior surface 24.

FIG. 3 illustrates a human eye 40 surrounded in front by an upper lid 42 and a lower lid 44. The eye 40 includes a segmented view of the cornea 46 and the iris 48, the circular pigmented membrane behind the cornea 46. FIG. 3 depicts eye 40 as it would appear after it has undergone extracapsular cataract extraction. The lens capsule 50 has a central opening in its anterior or forward wall and the lens, normally a bi-convex transparent body, has been removed and replaced by intraocular lens 10 of the present invention. The intraocular lens 10 is positioned on the posterior capsular membrane 30 of the lens capsule 50 adjacent to the vitreous humor 52, the clear colorless transparent jelly filling the portion of the eye posterior to the lens capsule 50.

The implanted intraocular lens 10 has its convex posterior or rear surface 32 in direction apposition with the posterior capsular membrane 30 of the lens capsule 50. The implanted lens 10 with its concave anterior surface 24 has less opportunity for contact within the pupillary space of the iris, significantly reducing the incidence of secondary complications following lens implantation. The annular space 38, which in one embodiment has a width of 3.5 millimeters between points 34 and 36, is sufficiently outside the optic region "d" of the eye's pupil to avoid causing any optical distortion. The direct apposition of the convex posterior surface 32 of the lens implant 10 reduces the cloudiness or opacity that occurs with the posterior capular membrane following extracapsular cataract extraction. However, in those situations which do call for secondary cataract surgery by discission of the posterior capsular membrane 30 of the capsule 50, a YAG laser can be directed to the annular space 38 for discission outside the optic region of the lens and eye. As described above, the geometry of the lens 10 stretches the posterior capsular membrane 30 and places it under a slight tension at the annular space 38 to facilitate the laser surgery or knife discission.

While the intraocular lens of the present invention has been described in detail herein, it will be evident that various and further modifications are possible without departing from the scope and spirit of the present invention.

I claim:

1. An intraocular lens for implantation in the capsular bag of an eye following extracapsular cataract extraction, comprising:

a lens body having an anterior surface extending to an edge that projects posteriorly at a predetermined angle and terminates in a plane, said lens body having a convex posterior surface projecting posteriorly beyond said plane of said edge; and haptics attached to said lens body for positioning said lens body within the capsular bag of the eye, wherein said convex posterior surface is adapted to be positioned in direct contact with an area of the posterior capsular membrane of the eye, thereby stretching and deforming the posterior capsular membrane into conformity with said convex posterior surface to improve visual acuity and to create a space between said edge, said area of contact, and the posterior capsular membrane to facilitate any laser surgery of the posterior capsular membrane required following implantation of the lens.

2. The intraocular lens of claim 1, wherein said anterior surface of said lens body is concave.

3. The intraocular lens of claim 1, wherein said anterior surface of said lens body is planar.

4. The intraocular lens of claim 1, wherein said anterior surface of said lens body is convex.

5. The intraocular lens of claim 1, wherein said posterior surface of said lens body has a radius of curvature such that said area of contact with the posterior capsular membrane accommodates the optic region of the eye.

6. The intraocular lens of claim 5, wherein said posterior surface of said lens body has a radius of curvature such that said area of contact with the posterior capsular membrane of the eye has a diameter between 2.5 and 4.5 millimeters.

7. The intraocular lens of claim 5, wherein said edge of said lens body is outside the optic region of the eye.

8. The intraocular lens of claim 1, wherein said haptics are a pair of flexible filament members attached to said lens body.

9. The intraocular lens of claim 8, wherein said haptics are adapted to be positioned inside the capsular bag to put the capsular bag in circumferential tension and to bias said lens body posteriorly into contact with the posterior capsular membrane.

10. The intraocular lens of claim 1, wherein said lens body is made from polymethylmethacrylate.

11. The intraocular lens of claim 1, wherein said lens body is a resilient material suitable for plastic deformation and injection through a small incision into the posterior chamber of the eye.

12. The intraocular lens of claim 1, wherein said edge extends around the circumferential perimeter of said lens body.

13. An intraocular lens for implantation in the capsular bag of the eye following extracapsular cataract extraction, comprising:
- a lens body comprising a convex posterior surface having an optic region and an anterior surface extending to a circumferential edge region projecting posteriorly and terminating in a plane, said circumferential edge region being outside said optic region and said convex posterior surface projecting posteriorly beyond said plane of said circumferential edge region; and
- haptics attached to said lens body for positioning said lens body in the capsular bag of the eye, wherein said convex posterior surface is adapted to be implanted in direct apposition with the posterior capsular membrane, thereby stretching and deforming the posterior capsular membrane into conformity with said convex posterior surface to improve visual acuity and to create an annular space between the posterior capsular membrane and said circumferential edge region to facilitate any laser surgery subsequently required of the posterior capsular membrane.

14. The intraocular lens of claim 13, wherein said convex posterior surface has a fixed radius of curvature and said anterior surface has a predetermined shape that determines the optical power of said lens body.

15. The intraocular lens of claim 14, wherein said anterior surface is concave.

16. The intraocular lens of claim 14, wherein said anterior surface is planar.

17. The intraocular lens of claim 14, wherein said anterior surface is convex.

18. The intraocular lens of claim 14, wherein said haptics are adapted to be positioned inside the capsular bag to put the capsular bag in circumferential tension and to bias said lens body posteriorly into contact with the posterior capsular membrane.

* * * * *